(12) United States Patent
Binmoeller et al.

(10) Patent No.: US 11,446,023 B2
(45) Date of Patent: Sep. 20, 2022

(54) HELICAL TISSUE ANCHOR DEVICE AND DELIVERY SYSTEM

(71) Applicants: Kenneth F. Binmoeller, Rancho Santa Fe, CA (US); Matthew Thomas Yurek, San Diego, CA (US); Michael P. Hartsfield, Poway, CA (US); John Greelis, Carlsbad, CO (US)

(72) Inventors: Kenneth F. Binmoeller, Rancho Santa Fe, CA (US); Matthew Thomas Yurek, San Diego, CA (US); Michael P. Hartsfield, Poway, CA (US); John Greelis, Carlsbad, CO (US)

( * ) Notice: Subject to any disclaimer, the term of this patent is extended or adjusted under 35 U.S.C. 154(b) by 0 days.

(21) Appl. No.: 16/832,131

(22) Filed: Mar. 27, 2020

(65) Prior Publication Data
US 2021/0401427 A1 Dec. 30, 2021

Related U.S. Application Data

(62) Division of application No. 15/661,613, filed on Jul. 27, 2017, now Pat. No. 10,639,031.

(51) Int. Cl.
*A61B 17/064* (2006.01)
*A61B 17/04* (2006.01)
(Continued)

(52) U.S. Cl.
CPC ............ *A61B 17/064* (2013.01); *A61B 1/018* (2013.01); *A61B 17/0401* (2013.01);
(Continued)

(58) Field of Classification Search
CPC ............ A61B 17/0401; A61B 17/0467; A61B 17/0487; A61B 17/064; A61B 17/07207;
(Continued)

(56) References Cited

U.S. PATENT DOCUMENTS

| 9,770,244 B2 | 9/2017 | Filiciotto |
| 2006/0030885 A1 | 2/2006 | Hyde |

(Continued)

FOREIGN PATENT DOCUMENTS

| CN | 103476348 A | 12/2013 |
| CN | 103476353 A | 12/2013 |

OTHER PUBLICATIONS

Extended European search report for European patent application No. 17835279.5, dated Apr. 15, 2021, 12 pages.
(Continued)

*Primary Examiner* — Mohamed G Gabr
(74) *Attorney, Agent, or Firm* — Mai-Tram D. Lauer; Westman, Champlin & Koehler, PA

(57) ABSTRACT

A delivery system for delivering a plurality of helical tissue anchors to repair a wall defect. Coaxially contained within the outer sheath are inner tubular members. The first inner tubular member designed to deploy a first helical tissue anchor, a second inner tubular member designed to deploy a second helical tissue anchor, and a centered inner tubular member contains a cinching mechanism. The two helical tissue anchors are connected to a suture or strap that pull the two helical tissue anchors together to close a tissue defect. A cinching mechanism holds the anchors and tissue defect together and cut the suture or strap.

6 Claims, 10 Drawing Sheets

(51) Int. Cl.
  *A61B 1/018* (2006.01)
  *A61B 17/072* (2006.01)
  *A61B 17/00* (2006.01)

(52) U.S. Cl.
  CPC ...... *A61B 17/0467* (2013.01); *A61B 17/0487* (2013.01); *A61B 17/07207* (2013.01); *A61B 2017/0034* (2013.01); *A61B 2017/0441* (2013.01); *A61B 2017/0464* (2013.01); *A61B 2017/0488* (2013.01); *A61B 2017/0649* (2013.01)

(58) Field of Classification Search
  CPC ............ A61B 1/018; A61B 2017/0034; A61B 2017/0441; A61B 2017/0488; A61B 2017/0649
  See application file for complete search history.

(56) References Cited

U.S. PATENT DOCUMENTS

| | | |
|---|---|---|
| 2007/0250020 A1 | 10/2007 | Kim et al. |
| 2008/0300629 A1* | 12/2008 | Surti .................. A61B 17/0487 606/232 |
| 2009/0287304 A1* | 11/2009 | Dahlgren ............ A61B 17/0401 623/2.37 |
| 2011/0166649 A1 | 7/2011 | Gross et al. |
| 2012/0083806 A1* | 4/2012 | Goertzen ........... A61B 17/0401 606/151 |
| 2012/0245604 A1* | 9/2012 | Tegzes ............... A61B 17/0401 606/151 |
| 2012/0283757 A1* | 11/2012 | Miller .................. A61F 2/2445 606/151 |
| 2013/0096672 A1* | 4/2013 | Reich .................. A61F 2/2457 623/2.11 |
| 2013/0334282 A1 | 12/2013 | Filiciotto |
| 2015/0351910 A1* | 12/2015 | Gilmore ............ A61B 17/0401 606/151 |
| 2018/0161033 A1 | 6/2018 | Filiciotto |

OTHER PUBLICATIONS

First Office Action, including search report, for Chinese patent application No. 201780059683.X, dated Feb. 9, 2022, 12 pages.
Notice of Reasons for Refusal for Japanese patent application No. 2019-503755, date drafted Apr. 22, 2021, 4 pages.
Decision of Refusal for Japanese patent application No. 2019-503755, date drafted Dec. 2, 2021, 4 pages.

* cited by examiner

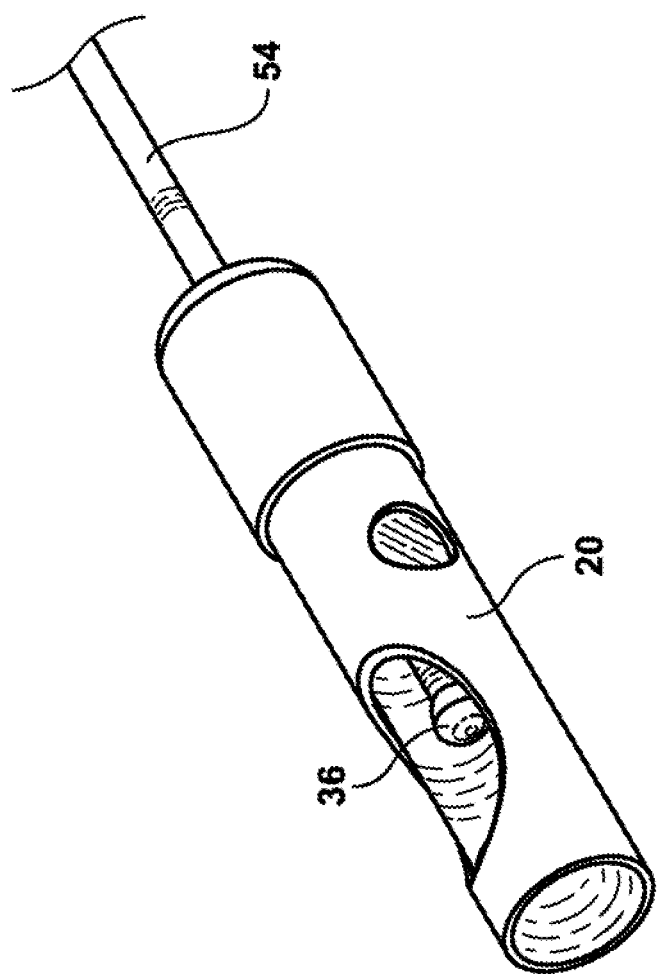
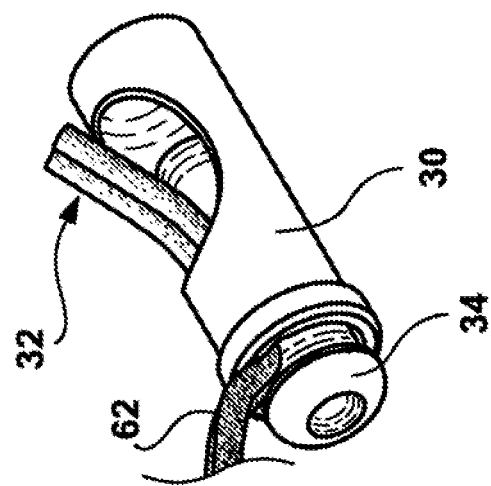
FIG. 6

HELICAL TISSUE ANCHOR DEVICE AND DELIVERY SYSTEM

RELATED APPLICATIONS

This patent application is a non-provisional of Provisional Application No. 62/367,592 filed on Jul. 27, 2016. This Provisional Application is incorporated by reference in its entirety.

FIELD OF THE INVENTION

This present invention relates to an apparatus and method for approximating or closing tissue defects with anchors that can be controlled independently of each other. More specifically, the present invention relates to a delivery system that deploys two or more anchoring elements through an endoscope. The device and methods also may be used for plicating or otherwise reconfiguring tissue and for fixation of tissue or other material to tissue.

BACKGROUND OF THE INVENTION

During a gastrointestinal endoscopic procedure, the operator often desires to repair or reconstruct a tear or defect or otherwise approximate or fixate tissue or other material by suturing.

Metallic clipping devices were first introduced for the primary purpose of achieving hemostasis of focal gastrointestinal bleeding. Indications for their use have expanded to include closure of perforations and fistulas, securing of catheters and stents, and as a marking device to direct endoscopic, surgical, and radiological therapy, among others. Several endoscopic clipping devices are commercially available. All consist of metallic double or triple prongs joined at the proximal end. The prongs of the clip are applied with pressure onto the target tissue and pinched closed by manually squeezing the catheter handle assembly. Clipping devices are limited by a fixed distance and relationship between the prongs.

The fixed distance between the prongs limits the operator's ability to close defects that exceed this distance, which limits applicability to small defects. The fixed relationship between the prongs limits the operator's ability to position the clip appropriately in relation to the area in need of treatment. For instance, the clips may not be able to close a defect that is approached tangentially at a curve or angle. Further, because the proximal ends of the legs are joined, the operator may not be able to adjust the positioning of one clip prong without affecting the positioning of the second. Positioning also may be limited because the clip may not be properly oriented when it is deployed or the clip may slip out of alignment during application. Finally, the legs of presently-used clips must be actuated and anchored at the same time. If unequal pressure is applied to the legs during anchoring, closure may be sub-therapeutic and scissoring of the legs may occur that can result in tissue damage. Presently-used clips are only capable of capturing the mucosa and do not penetrate into the deeper wall layers (submucosa and muscular propria layers).

A suturing device that addresses the limitations of clips is the Apollo Overstitch. This device provides a curved needle movable on an arm to pierce tissue and perform tissue approximation and suturing. This device is capable of full-thickness (entire bowel wall) tissue capture and the closure of larger defects, however, the device cannot be delivered through the working (operative) channel of the endoscope and must be pre-mounted on the end of the endoscope. It also involves multiple time consuming, technically demanding maneuvers and manipulations. A need remains for an endoscopic tissue closure device which addresses the limitations of presently-used clips and is capable of full thickness tissue capture.

The Ovesco "over-the-scope-clip" (OTSC) can achieve full-thickness closure of a defect by suctioning tissue into a cap attachment mounted on the end of the endoscope. The clip, mounted on the cap attachment, is released by turning a hand wheel, similar to band ligation. The size of the defect that can be closed is small, limited by the diameter of the cap attachment. Like the Apollo Overstitch, the OTSC must be pre-mounted onto the endoscope prior to use.

Accordingly, it would be desirable to obtain a multiple tissue anchor and delivery system for facilitating the repair of wall defects, plication of tissue, and treatment of lesions delivered through the working channel of the endoscope.

It would also be desirable to obtain a multiple tissue anchor and delivery system for repairing wall defects, plicating tissue, and treating lesions whereby the apparatus and methods have the capability to facilitate repairs of defects of any size, plicate tissue of any size, and treat lesions of any size, with deployment of each anchor independent of one another under direct endoscopic visualization.

It would also be desirable to obtain a multiple tissue anchor and delivery system to provide treatment of relatively large perforations, lesions and damage areas under endoscopic visualization.

SUMMARY OF THE INVENTION

The present invention comprises a novel delivery system for delivering two or more helical anchors through an endoscope or colonoscope to repair a wall defect, plicate tissue, or treat a lesion. The delivery system comprises an outer sheath tubular member designed to pass through the working channel of an endoscope.

Coaxially contained within the outer sheath tubular member are three individual inner tubular members; a first inner tubular member being designed to deploy a first helical tissue anchor (sometimes referred to as the "first helical device" hereinafter), a second inner tubular member being designed to deploy a second helical tissue anchor (sometimes referred to as the "second helical device" hereinafter"), and a third centered inner tubular member containing a retraction member. The first inner tubular member coaxially contains a first reinforced tubular member that allows rotational manipulation of the first helical tissue anchor designed to be embedded into the wall tissue. The first inner tubular member also has a lumen whereby a first control wire is coaxially enclosed within that functions to release the first helical anchor. After the first helical tissue anchor is embedded into the wall tissues, it is released and the first control wire is retracted distally. The second inner tubular member coaxially contains a second reinforced tubular member that allows rotational manipulation of the second helical tissue anchor to be embedded into the wall tissue. The second inner tubular member also has a lumen whereby a second control wire is coaxially enclosed within that functions to release the second helical tissue anchor. After the second helical tissue anchor is embedded into the wall tissues, it is released and the second control wire is retracted distally. Attached to the first helical tissue anchor and to the second helical tissue anchor is a strap or suture mechanism that is contained within the third central inner tubular member.

The strap or suture member is engaged to the third central inner tubular member that when moved distally causes the suture member to become tightened between the first and second helical tissue anchors, compelling the two helical tissue anchors together and partially or fully closing the treatment area.

A novel handle assembly can be attached to the distal end of the outer sheath tubular member which engages the first inner tubular member, the second inner tubular member, and the third inner central tubular member. The handle assembly includes a plurality of rotating thumbwheels, slide buttons and release mechanisms.

In clinical operation, the access to and visualization of the treatment area is first conducted using standard endoscopy techniques. The clinician passes the multiple helical tissue anchors/inner tubular member and delivery system through the working channel of the endoscope.

To engage one side of the lesion area, the clinician advances one of the thumb slides forward advancing the first tissue helical anchor and its delivery catheter out of the distal end of the outer catheter sheath. The first helical device and its delivery catheter can be visualized endoscopically. The clinician manipulates the endoscope and maneuvers the first helical tissue anchor and its delivery catheter by sliding the ratcheting thumb slide forward to position the first helical tissue anchor against the target site and then rotates the thumbwheel to embed the first helical device into the mucosal, submucosal or muscle tissue as desired. After the first helical device is satisfactorily embedded into the tissue, the clinician retracts the release mechanism to release the first helical device. This is accomplished by pulling back on the release mechanism behind the ratcheting thumb slide. Once the first helical device is released, pushing the central button on the thumb slide down releases the thumb slide from the ratchet teeth allowing it to be pulled proximally along with the release mechanism. Retracting the thumb slide back pulls the delivery catheter back into the sheath of the helical device leaving the first helical device and attached strap or suture in the tissue.

The clinician then engages the other side of the lesion by advancing the other thumb slide forward to advance the second helical tissue anchor and its delivery catheter out of the distal end of the catheter shaft. The second helical tissue anchor and its delivery catheter can be visualized endoscopically. The clinician manipulates the endoscope and maneuvers the second helical device and its delivery catheter to position the second helical tissue anchor against the target site and then rotates the thumbwheel to embed the second helical device into the mucosal, submucosal, or muscle layer of the wall as desired. After the second helical device is satisfactorily embedded into the tissue, the clinician retracts back on the release mechanism to release the second helical device. This is accomplished by pulling back on the release mechanism behind the ratcheting thumb slide. Once the second helical device is released, pushing the central button on the second thumb slide down releases the thumb slide from the ratchet teeth, allowing it to be pulled proximally. Retracting the thumb slide pulls the delivery catheter back into the sheath of the helical device leaving the second helical device and attached strap or suture in the tissue.

The clinician then advances the central inner tube to pull the two helical devices and their attached tissues together. A ferrell, bolo tie, locking anchor, spring clip or a preformed knot and knot pusher locks the two helical tissue anchors together to partially or fully close the treatment area.

There are two embodiments that perform the same tissue approximation with the anchor and delivery system, but differ in the inner delivery catheter mechanisms.

The first embodiment has a single lumen sheath with three elements running throughout its length. Two tubular elements engage the connector, coupler and anchor components. A third tubular element functions to manipulate the strap or suture held by a wire that extends proximally through the handle. After delivery of the anchors, the two tubular elements of the delivery systems are retracted out of the sheath and a knot pusher or ferrel is pushed over the third element and suture or strap tether moving and locking the anchors together closing the tissue opening.

In the second embodiment, the sheath has a multi-lumen configuration that contains three or four individual lumens that are designed to each contain the three elements and one for the suture or strap. Two lumens of the sheath function to operate the helical devices. The third and fourth lumens contains the suture or strap assembly and a locking mechanism. The third and fourth lumen maybe combined further reducing the catheters profile. The delivery procedures between the two embodiments are similar whereby the second embodiment advancement of the third element is accomplished by advancing the sheath itself. The second embodiment with independent lumens in the sheath for the suture or strap element reduces the potential for twisting around the helical device delivery elements. The third element with its locking mechanism is similar between the two embodiments whereby they similarly pull on the suture or strap closing the tissue opening. After placement of the catheter tip bringing the tissues together, a handle element is pulled to first pinch and lock the suture or strap element and then to cut it. The delivery system is then removed through the endoscope.

BRIEF DESCRIPTION OF THE DRAWINGS

FIG. 6 is a perspective view of the suture cinching and excising inner tubular member and the third intermediary inner tubular member whereby the distal and proximal sections have been separated from each other by retraction of the distal cap ball mechanism and wherein retraction of the proximal section cuts the sutures or strap.

Corresponding reference characters indicate corresponding parts throughout the several views. The exemplifications set out herein illustrate exemplary embodiments of the invention, and such exemplifications are not to be construed as limiting the scope of the invention in any manner.

DESCRIPTION OF THE PREFERRED EMBODIMENTS

Figure 1:
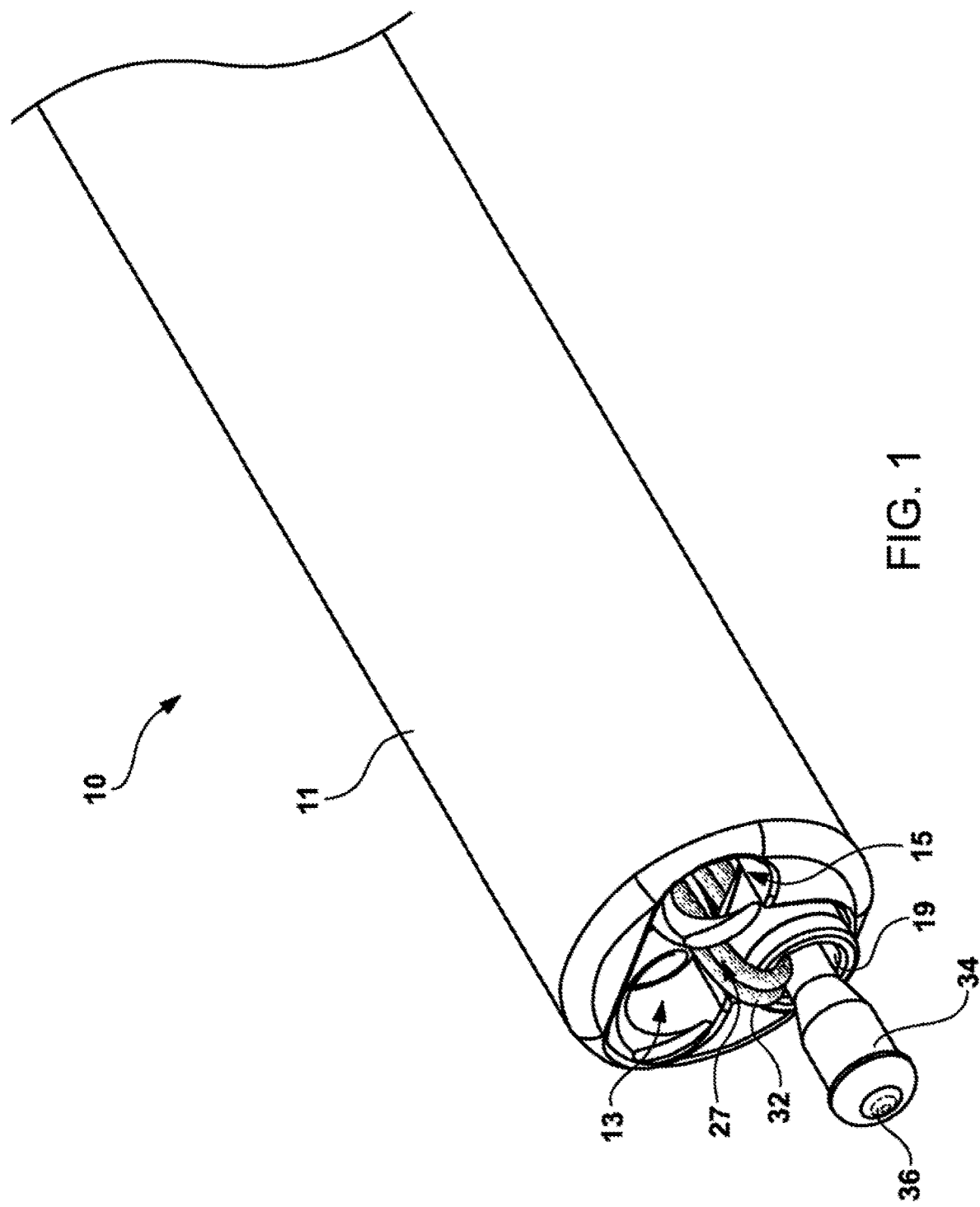
FIG. 1 is a perspective view of the distal end of the catheter system showing the multi-lumen catheter showing the first and second inner tubular members which correspond to the first and second helical anchors and a third inner tubular member showing the cinching devise and a fourth inner tubular member with the suture strap mechanism engaged to the proximal end of an elongated shaft.

Referring now to the drawings and particularly to FIG. 1 which is a perspective view of the present invention 10 which includes a distal end of the catheter system showing the multi-lumen catheter 11, a first inner tubular lumen 13 and second inner tubular lumen 15 which correspond to the first and second helical tissue anchors and associated shaft members and a third and fourth inner tubular lumen 19 and 27 with the suture strap and cinching mechanism engaged to the proximal ends of elongated shaft that travels throughout the length of the multi-lumen catheter and terminates in a connection to the handle mechanism 70.

The multi-lumen catheter can be fabricated from a number of polymeric materials, such as polytetrafluoroethylene (PTFE), FEP, ETFE, polyvinyl chloride (PVC), polyethylene, polypropylene, PEEK, polybutylene, acryaontirile-butadiene-styrene (ABS), rubber modified styrene, polyacetal, polyethylene, graphite or nylon, or a combination of metal coil or braid encapsulated in the polymeric materials or any combination thereof. The diameter of the first inner tubular lumen 13 and the second inner tubular lumen 15 is in the range of 0.25 mm to 1.2 mm, with a preferred diameter of 0.5 mm. The multi-lumen catheter 11 can have a length in the range of 100 to 500 cm depending on the clinical application.

Figure 2:
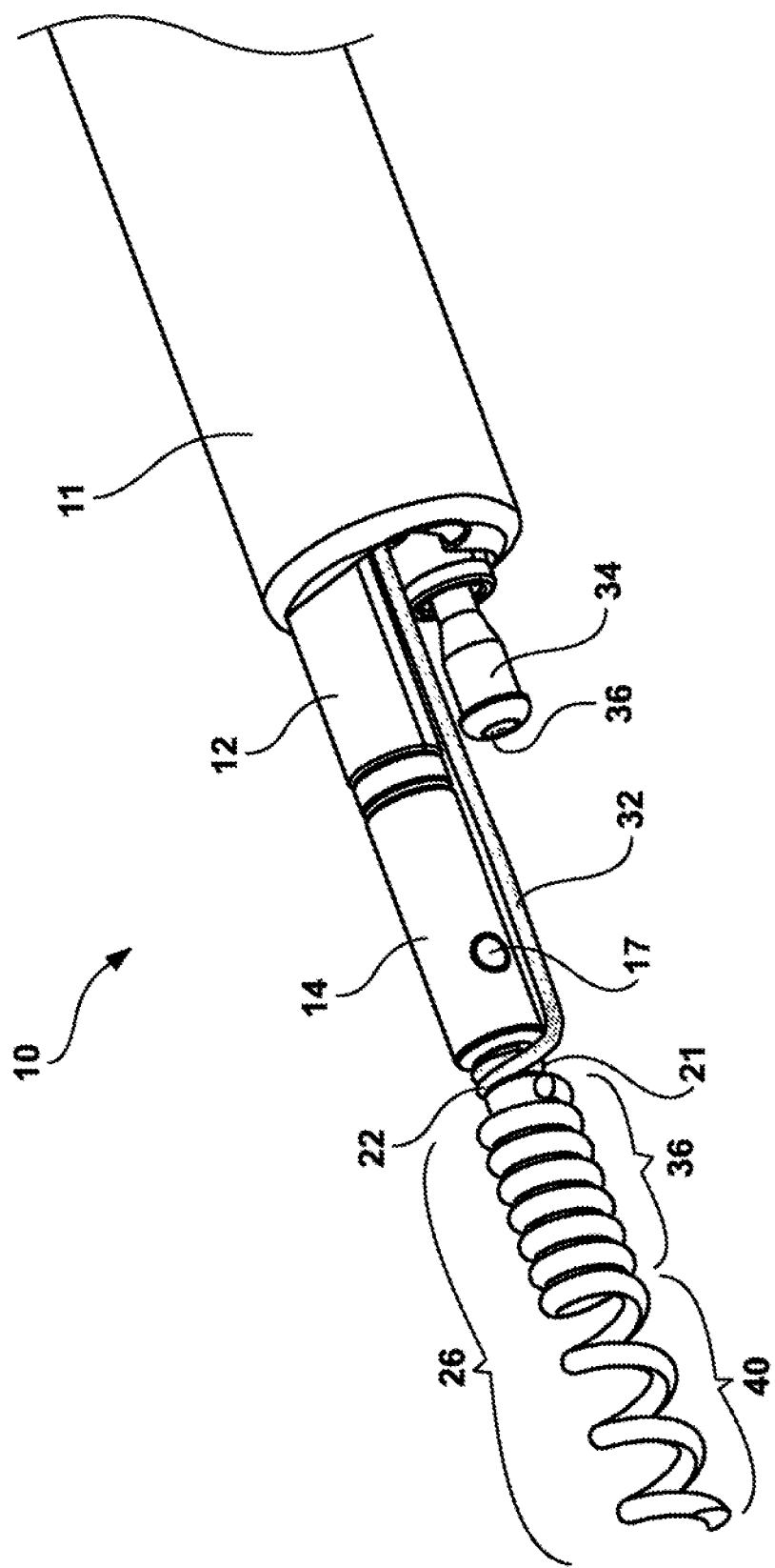
FIG. 2 is a perspective view of the distal end of the helical tissue anchor delivery system showing first helical tissue anchor assembly projecting distally outward of the multi-tubular catheter shaft.
Figure 8:
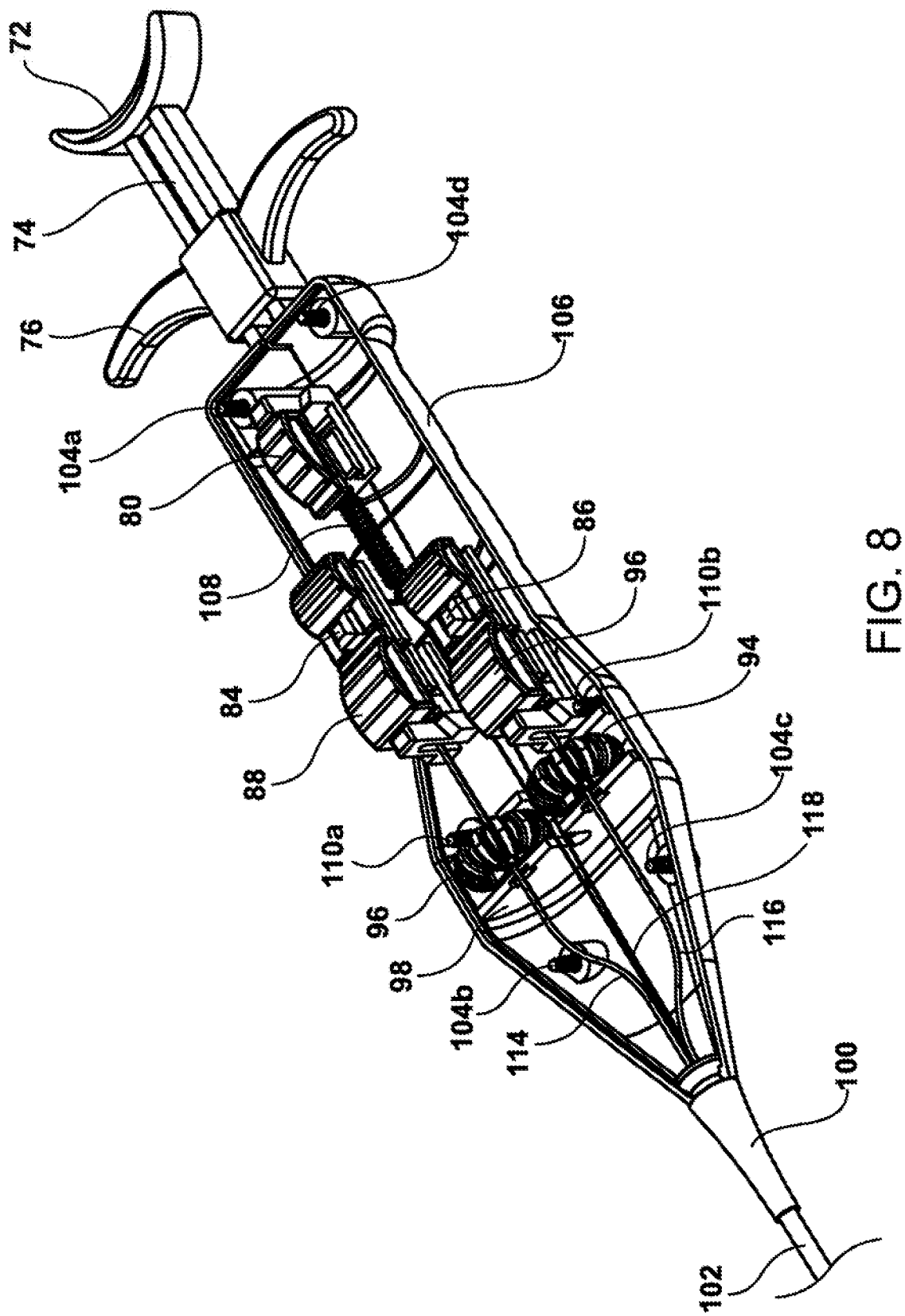
FIG. 8 is a perspective inner view of the proximal handle mechanism with the top body member removed, showing the components and interaction with tubular members.

Now referring to FIGS. 2 and 8, coaxially aligned within the first inner tubular lumen 13 is a first elongated shaft 114 (see FIG. 8) that travels throughout the length of the multi-lumen catheter and terminates in a connection to the handle mechanism 70. The elongated shaft 114 has a series of components that are designed to have a removable component 14 on its distal end. On the distal end of the elongated shaft 114 is a fixed engagement member 12 that coaxially removably engages a first removable anchor engagement member 14. Not shown is a fork configured mechanism that extends from the distal end of the first engagement member 12 to become coaxially inserted into the first removable anchor coupler member 14. On the surface of each fork configuration member, is a tab that become inserted into the hole in the first removable anchor coupler member 14. The first connection tab with corresponding hole/tab assembly 17 is used to removably affix the first engagement member 12 to the first removable anchor coupler member 14.

Attached to the distal end of the first removable anchor engagement member is first helical tissue anchor 26. First helical tissue anchor 26 has two different winds or thread pitch where the coils are in a tight configuration 36 on the proximal end and have a relatively loose configuration 40 on its distal end. The relatively loose configuration 40 is designed to utilize rotational forces to embed the first helical tissue anchor 26 into the mucosal, submucosal or muscle tissues. It is anticipated by the Applicants that the tight configuration 46 can be appropriately shortened in length to minimize this tight configuration from protruding from the treated tissue area. Also, the depth of tissue anchor capture can be adjusted when embedding the first tissue helical anchor to enable full-thickness tissue closure and full-thickness plication. Located between the first helical tissue anchor 26 and the first removable anchor engagement member 14 is a suture connection area 21 whereby a suture strap mechanism 22 is affixed by a series of rotations around the suture connected area 21. The suture mechanism strap mechanism 22 is designed to allow proximal section of first helical tissue anchor shaft 114, first connector member 12, first removable anchor coupler member 14 and first helical tissue anchor 26 to rotate without the suture strap mechanism rotating. The diameter of the first connection member 12 and the first removable anchor coupler member is in the range of 0.25 mm to 1.2 mm, with a preferred diameter of 0.5 mm. First fixed engagement member 12 and first removable anchor engagement member 14 can be fabricated from metallic materials such as brass, brass alloys, stainless steel, cobalt chrome alloys, nickel titanium, copper alloys or polymer suture materials both resorbable and non-resorbable, such as nylon, polypropylene, polyethylene, Kevlar, polyurethane, lactic acid, polycaprolactone, or metallic materials such as brass, brass alloys, stainless steel, cobalt chrome alloys, nickel titanium, copper alloys or any combination thereof, or any combination thereof or polymeric materials, such as polyvinyl chloride (PVC), polyethylene, polypropylene, PEEK, Ultem, polybutylene, acryaontirile-butadiene-styrene (ABS), rubber modified styrene, polyacetal, polyethylene, graphite, polyurethane or nylon, or any combination thereof.

The suture strap mechanism 22 can be a mono-strand or multi-strand configuration and can be fabricated from a number of polymer suture materials both resorbable and non-resorbable, such as nylon, polypropylene, polyethylene, Kevlar, polyurethane, lactic acid, polycaprolactone, or metallic materials such as brass, brass alloys, stainless steel, cobalt chrome alloys, nickel titanium, copper alloys or any combination thereof, or any combination thereof or polymeric materials, such as polyvinyl chloride (PVC), polyethylene, polypropylene, PEEK, polybutylene, acryaontirile-butadiene-styrene (ABS), rubber modified styrene, polyacetal, polyethylene, graphite, polyurethane or nylon, or any combination thereof.

Also shown in FIG. 2 is third inner tubular member cinching mechanism 34 and retraction ball mechanism 36 which is engaged to third connection shaft 54.

Figure 3:
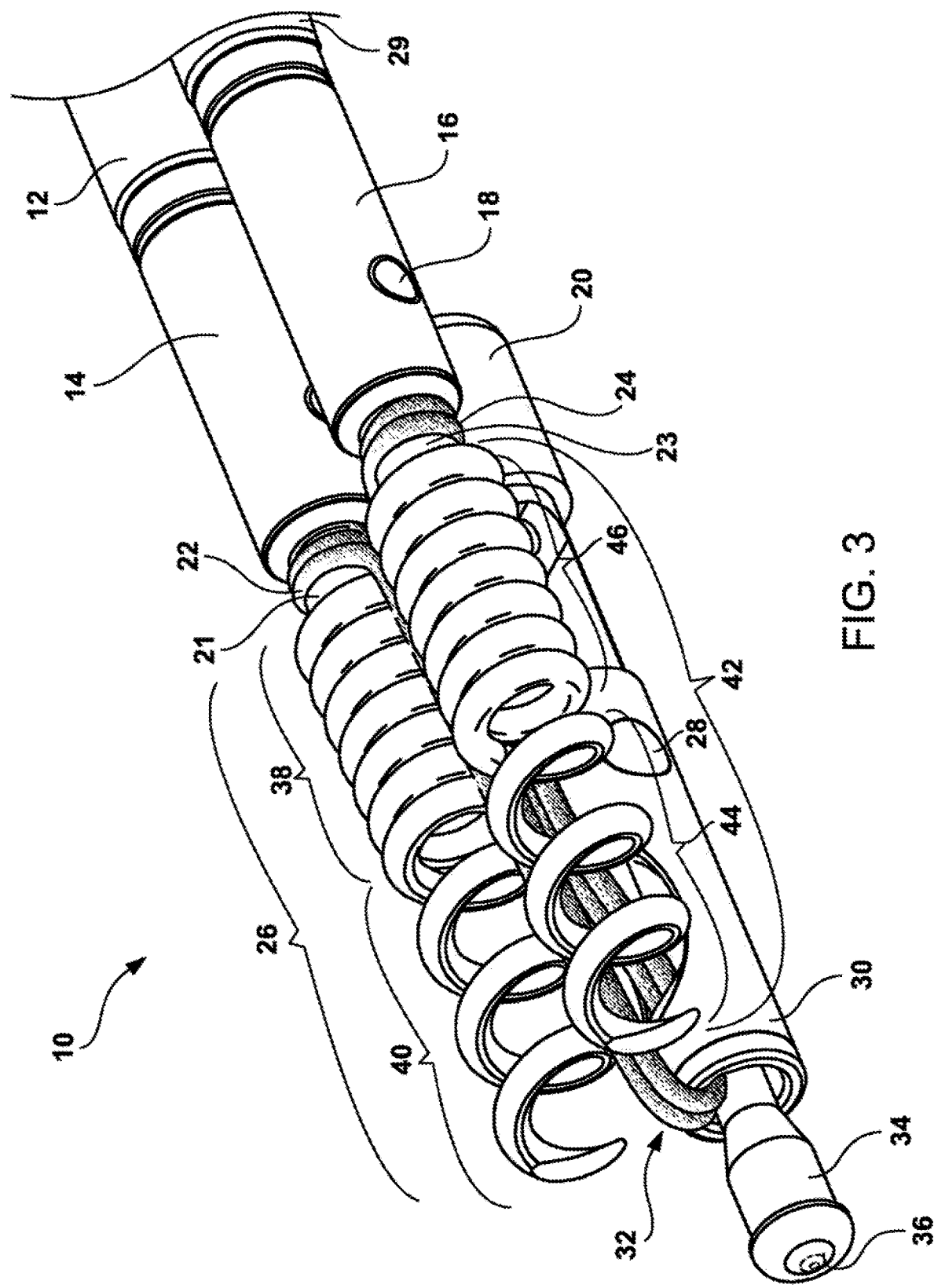
FIG. 3 is perspective inner view of the distal end of the helical tissue anchor delivery system showing the first and second anchor assemblies and the suture cinching and excising inner tubular member with the multi-tubular catheter shaft removed.

Now referring to FIGS. 3 and 8, which show an inner perspective view of the distal end of the helical tissue anchor delivery system showing the first and second anchor assemblies and the suture cinching and excising inner tubular member. The first anchor deployment assembly was described the paragraph above this paragraph will focus primarily on the second anchor deployment assembly.

Coaxially aligned within the second inner tubular lumen 15 is a second elongated shaft 116 that travels throughout the length of the multi-lumen catheter and terminates in a connection to the handle mechanism 70. The second elongated shaft 116 has a series of components that are designed to have a second removable anchor coupler member removable 16 on its distal end. On the distal end of the elongated shaft 116 is a second fixed engagement member that coaxially removable engages a second removable anchor engagement member 16. Not shown is a fork configured mechanism that extends from the distal end of the second engagement member 29 to become coaxially inserted into the first removable anchor coupler member 16. On the surface of each fork configuration member, is a tab that become inserted into the hole in the second removable anchor coupler member 16. The second connection tab with corresponding hole/tab assembly 18 is used to removably affix the second engagement member 29 to the second removable anchor coupler member 16.

Attached to the distal end of the second removable anchor engagement member is second helical tissue anchor 42. Second helical tissue anchor 42 has two different winds or thread pitch where the coils are in a tight configuration 46 on the proximal end and have a relatively loose configuration 44 on its distal end. The relatively loose configuration 44 is designed to utilize rotational forces to embed the second helical anchor 42 into the mucosal, submucosal or muscle tissues. It is anticipated by the Applicants that the tight configuration 46 can be appropriately shortened in length to minimize this tight configuration from protruding from the treated tissue area. Also, the depth of tissue capture can be adjusted when embedding the second helical tissue anchor to enable full-thickness tissue closure and full-thickness plication. Located between the second helical tissue anchor 42 and the second removable anchor engagement member 16 is a second suture connection area 23 whereby a suture strap mechanism 22 is affixed by a series of rotations around the second suture connected area 23. The suture mechanism strap mechanism 22 is designed to allow proximal section of second tissue anchor shaft 116, second connector member 29, second removable anchor coupler member 16 and second helical tissue anchor 42 to rotate without the suture strap mechanism rotating. Second fixed engagement member 29 and second removable anchor engagement member 16 can be fabricated from metallic materials such as brass, brass alloys, stainless steel, cobalt chrome alloys, nickel titanium, copper alloys or polymer suture materials both resorbable and non-resorbable, such as nylon, polypropylene, polyethylene, Kevlar, polyurethane, lactic acid, polycaprolactone, or metallic materials such as brass, brass alloys, stainless steel, cobalt chrome alloys, nickel titanium, copper alloys or any combination thereof, or any combination thereof or polymeric materials, such as polyvinyl chloride (PVC), polyethylene, polypropylene, PEEK, polybutylene, acryaontirile-butadiene-styrene (ABS), rubber modified styrene, polyacetal, polyethylene, graphite, polyurethane or nylon, or any combination thereof.

Also shown in FIGS. 3 and 8 are the third suture cinching and excising inner tubular member 30 of the proximally located single suture strap mechanism 118 in an extended configuration with the third inner tubular cinching mechanism extended out of the distal end of the suture cinching and excising inner tubular member 30 and with retraction ball mechanism 36. The pair of suture strap mechanisms 32 extend out of the third suture cinching and excising inner tubular member 30 and are attached as described above to first and second suture connection areas. The other end of the pair of suture strap mechanism penetrates a window 50 in the distal end that extends proximally toward the handle and at a proximal location (not shown) forming a loop that engages a proximally located single suture strap mechanism 118 that extends proximally down the catheter lumen to the handle 70. Also shown is an interference catching mechanism 28 that is designed to engage the retraction ball mechanism 36 and retract the suture cinching and excising tubular member 30 proximally back. When the third suture cinching and excising inner tubular member 30 is further retracted proximally, the pair of suture strap mechanisms 32 is cut by the sharp distal end of the window 50 in the third suture cinching and excising inner tubular member 30.

Figure 4:
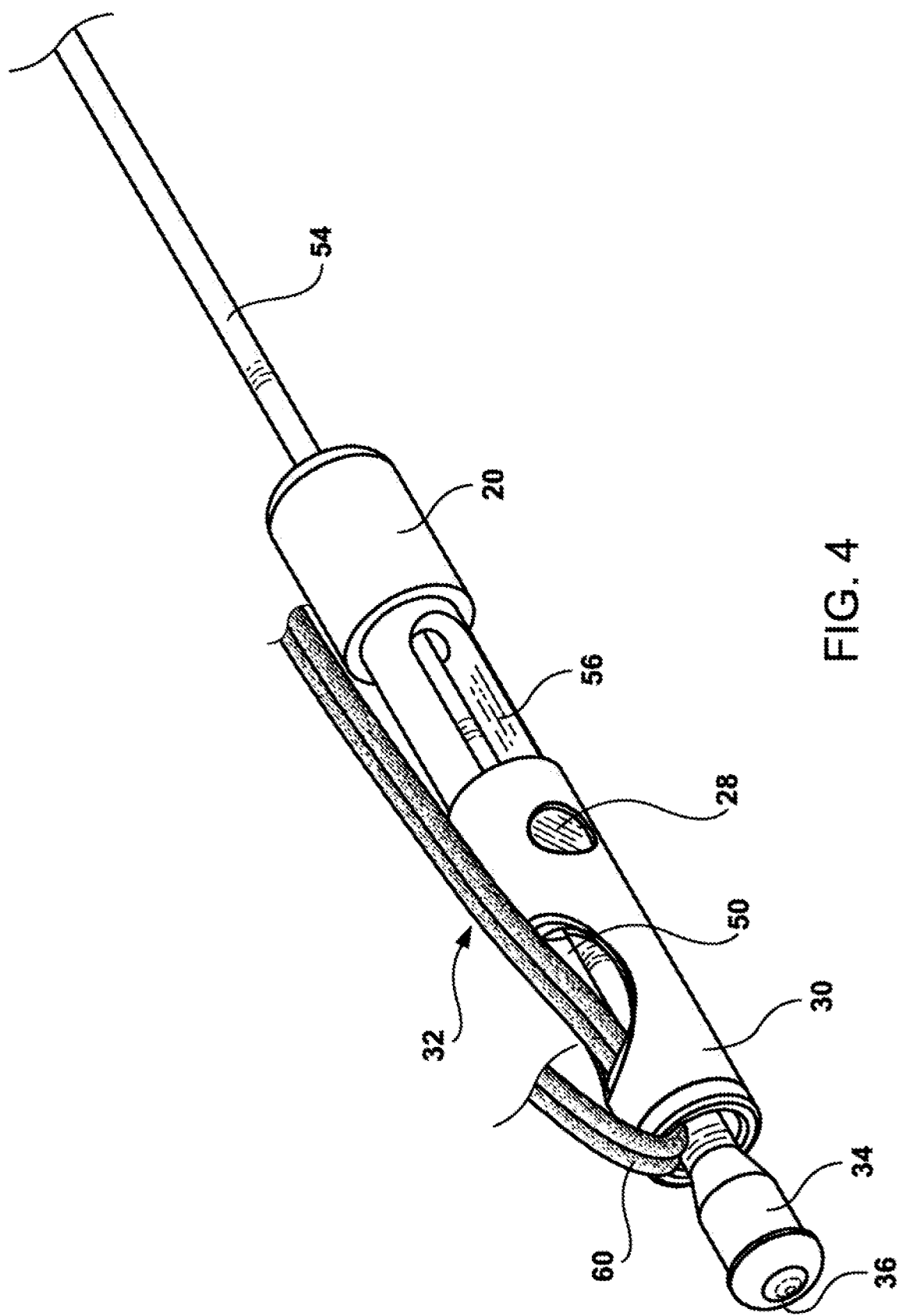
FIG. 4 is a perspective view of the suture cinching and excising inner tubular member having a distal section coaxially engaged to a third intermediary inner tubular member where by both are coaxially engaged to an elongated shaft member.

Now referring to FIG. 4 which shows a perspective view of the suture cinching and excising inner tubular member 30 having a distal section coaxially engaged to a proximal third intermediary inner tubular member 20 where by both are coaxially engaged to the distal section of the elongated shaft member 54. The distal end 54 connects to the elongated shaft 118 and extends the catheter lumen to the handle assembly 70. On the proximal end is the third intermediary inner tubular member 20 the distally includes a pair of forks 56. The forks are designed to guide interference catching mechanism 28. The window 50 in the third distal inner tubular member 30 is clearly shown with the pair of suture strap mechanism 32 traveling through the window 50, out the distal end 60 which continues to the first suture strap mechanism connection area 21 and second suture strap mechanism connected area 23.

Figure 5:
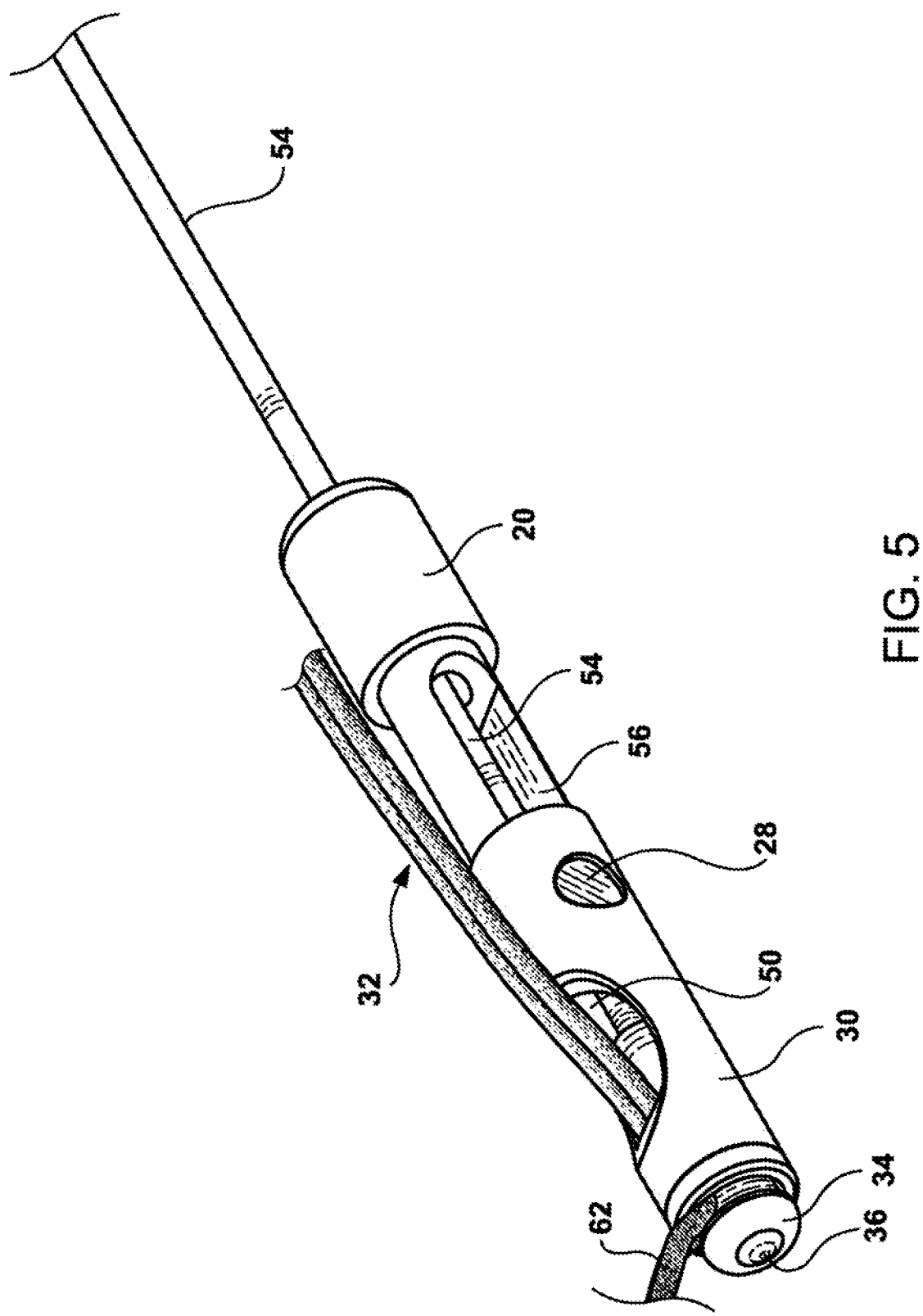
FIG. 5 is a perspective view of the suture cinching and excising inner tubular member and third intermediary inner tubular member whereby the distal cap is retracted causing the suture to become cinched between the distal cap and the distal section.

Shown in the perspective view of FIG. 5, is the suture cinching and excising inner tubular member 30 and third intermediary inner tubular member 20 whereby the distal cap 34 is retracted causing the pair of sutures strap mechanism 62 to become cinched between the distal cap 34 and the distal end of the suture cinching and excising inner tubular member 30.

In FIG. 6, shown is a perspective view of the suture cinching and excising inner tubular member 30 and third intermediary inner tubular member 20 whereby the distal and proximal sections have been separated from each other by retraction of the distal cap ball mechanism 36 and wherein retraction of the proximal section cuts the sutures. The incising of the suture strap mechanism generally occurs after the first helical tissue anchor 26 and second helical tissue anchor 42 have been embedded into the mucosal tissue layers and the defect in the wall has been closed by biasing the first helical tissue anchor 26 and second helical tissue anchor 42 toward each other.

Figure 7:
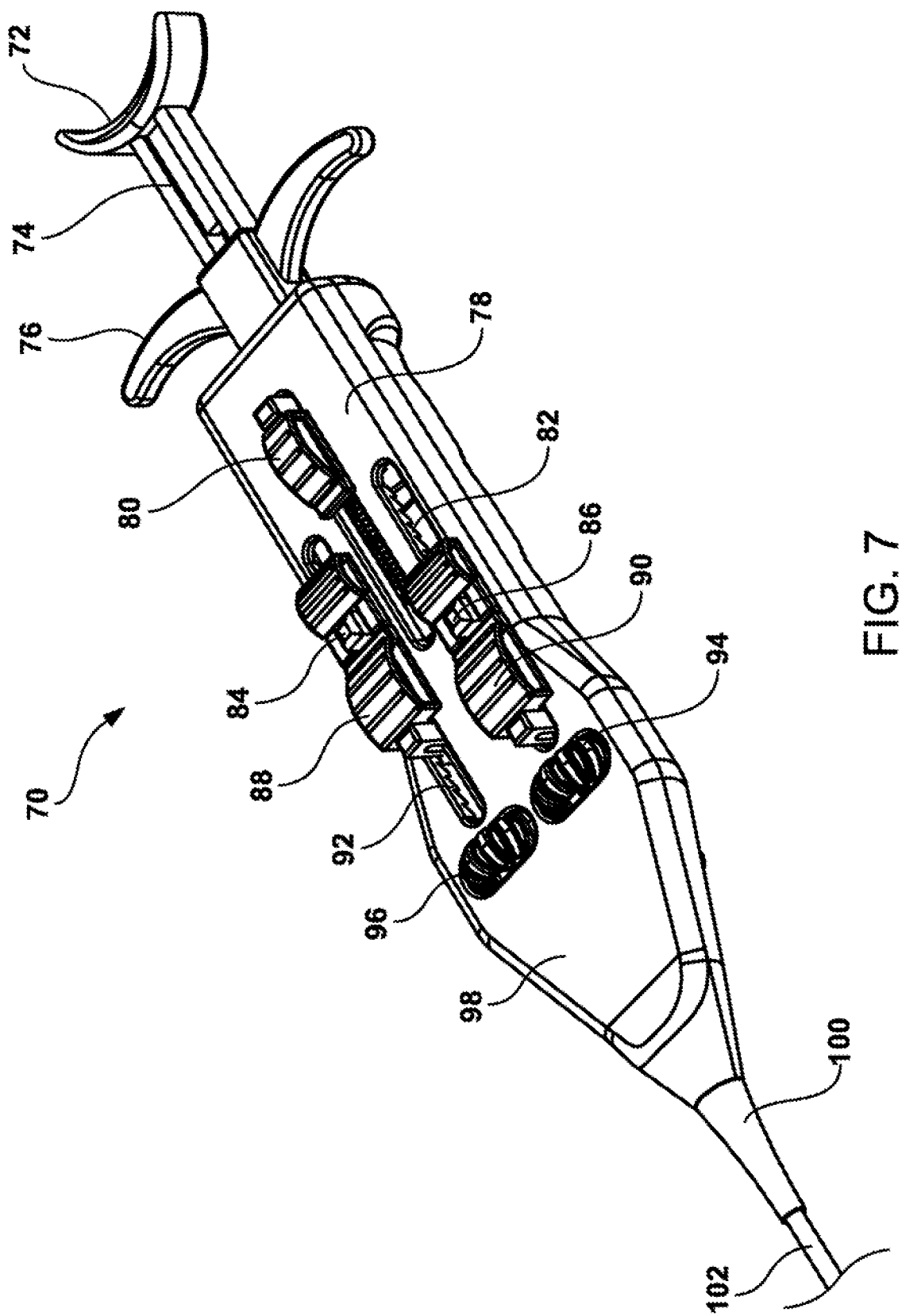
FIG. 7 is a perspective top view of the proximal handle mechanism showing the overall design and configuration of channels.

FIG. 7 is a perspective view of the handle mechanism 70 having a body 78 that comprises a clam shell design. The clam shell design has a top section and a bottom section that felicitate the fabrication and placement of the handle components within the handle mechanism 70. The handle mechanism 70 has a pair of thumbwheels 96, 94 for producing rotational forces to the inner tubular members 114, 116 respectively, with distally mounted helical tissue anchors 26, 42. Included is a first slide button 88 for advancing and retracting the first inner tubular member 114, and a first release button 84 for disengaging the first helical tissue anchor 26. Also included is a second slide button 90 for advancing and retracting the second inner tubular member 116, and a second release button 86 for disengaging the second helical tissue anchor 42. Attached and engaged to the distal end of the handle body 78 is the proximal end of the outer sheath 102 with strain release mechanism 100.

The first inner tubular member 114, at the sheath strain relief 100, enters the handle body 78 from its originating distal end whereby the outer surface of the first inner tubular member 114 is engaged to the first thumbwheel 96 allowing for rotational movement and embedment of the first helical tissue anchor 26. The first inner tubular member 114 is further engaged to the first slide mechanism 88 for advancing and retracting the first tubular member 114 within the sheath and for maneuvering its proximal end with first helical tissue anchor 26, towards the desired treatment site. The first release button 84 is also engaged to the first inner tubular member's stylus for releasing the first helical tissue anchor 26 after embedment in the tissue.

The second inner tubular member 116, at the sheath strain relief, 100 enters the handle body 78 from its distal end whereby the outer surface of the second inner tubular member 116 is engaged to the second thumbwheel 94 allowing for rotational movement for embedment of the second helical tissue anchor 42. The second inner tubular member 116 is further engaged to the second slide mechanism 90 for advancing and retracting the second tubular member 116 within the sheath and for maneuvering its proximal end with second helical tissue anchor 42, towards the desired treatment site. The second release button 86 is also engaged to the second inner tubular member's stylus for releasing the second helical tissue anchor 42 after embedment in the tissue.

The handle body 78, the pair of thumbwheels 94, 96, the pair of slide buttons 86, 88 and the pair or release buttons 84, 86 all can be fabricated from a number of polymeric materials, such as polyvinyl chloride (PVC), polyethylene, polypropylene, PEEK, polybutylene, acryaontirile-butadiene-styrene (ABS), rubber modified styrene, polyacetal, polyethylene, polyurethane or nylon, or any combination thereof.

FIG. 8 is a perspective top view of the bottom section 106 of the handle mechanism 70 showing the overall design and configuration of channels. In this figure, the upper clam shell component has been removed and a better view of all the internal components is shown. The handle mechanism 70 is a clam shell design that facilitates the assembly process for placing and locating the various components. The upper section and lower section of the claim shell design can be attached to each other using general adhesive, snap fit or screw technology. At the proximal end of the handle mechanism 70 is a proximal retraction member 72 with proximal member shaft 74 and proximal retraction finger grips. Positioned in specific locations are the first, second, third and fourth clam shell connection means 104a, 104b, 104c, 104d. Also positioned in a strategic location is the first and second clam shell alignment tab 110a and 110b. The third slide button 80 is engaged to spring mechanism 108 and the top half of the handle 78 to apply tension to the suture strap mechanism. The single suture strap mechanism 118, enters from the strain relief 100 and is positioned by the alignment bridge 98, and enclosed by the spring mechanism 108 near the its connection to the third slide button 80. The proximal section of the first inner tubular member 114 enters from the strain relief 100, is positioned by an alignment bridge 98 to the first tissue anchor thumbwheel 96. The outer surface of the first inner tubular member 114 is engaged to the lumen of the first tissue anchor thumbwheel 96 by adhesive or press fit such that rotation of the first tissue anchor thumbwheel imparts a likewise rotational force on the first inner tubular member 114 and onward to the first tissue anchor 26. The first inner tubular member 114 terminates engaged to the first slide button 88. The proximal section of the second inner tubular member 116 enters from the strain relief 100, is positioned by an alignment bridge 98 to the second tissue anchor thumbwheel 94. The outer surface of the second inner tubular member 116 is engaged to the lumen of the first tissue anchor thumbwheel 94 by adhesive or press fit such that rotation of the first tissue anchor thumbwheel 94 imparts a likewise rotational force on the second inner tubular member 116 and onward to the second tissue anchor 42. The second inner tubular member 116 terminates engaged to the second slide button 96.

Figure 9:
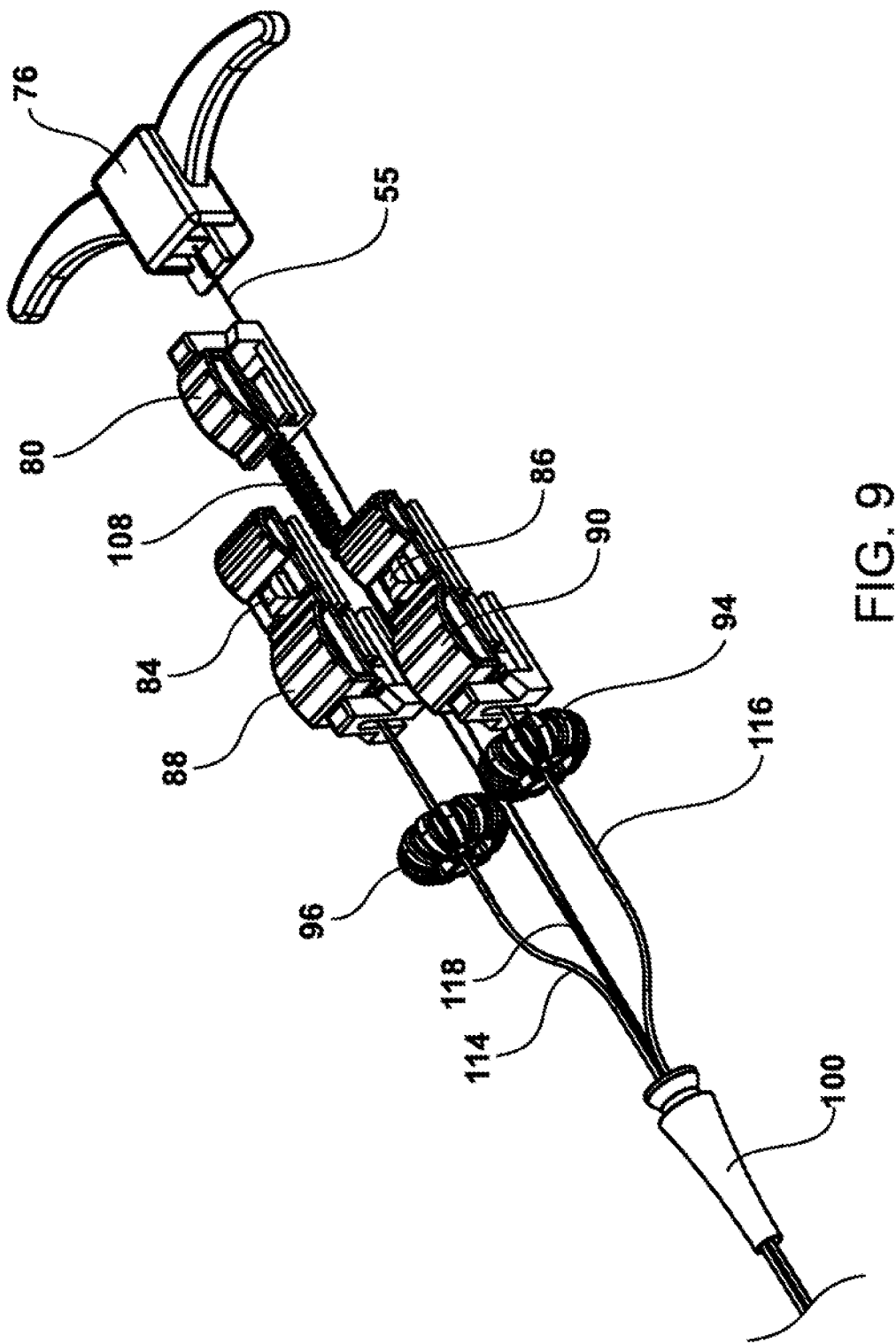
FIG. 9 is a perspective skeleton view of components of the proximal handle mechanism with the top and bottom body members removed and further showing the components and interaction with tubular members.

FIG. 9 is a perspective skeleton view of components of the proximal handle mechanism with the top and bottom body members removed and further showing the main components and interaction with tubular members. Exiting the strain relief 100 are the first inner tubular member 114, the second inner tubular member 116, the cinching member 55 and the single suture strap mechanism 118. Also shown is first inner tubular member 114 passing through, and attached to, a lumen of the first thumbwheel 96 and the second inner tubular member 116 passing through, and attached to, a lumen of the second thumbwheel 94. The terminal end of the first inner tubular member 114 is attached to the first slide 88 and the second inner tubular member 116 is attached to the second slide 90. The third single suture strap mechanism 118 passing through a spring mechanism 108 and terminates at third slide mechanism 80 and the cinching member 55 is attached to the proximal retraction handle 76.

Figure 10:
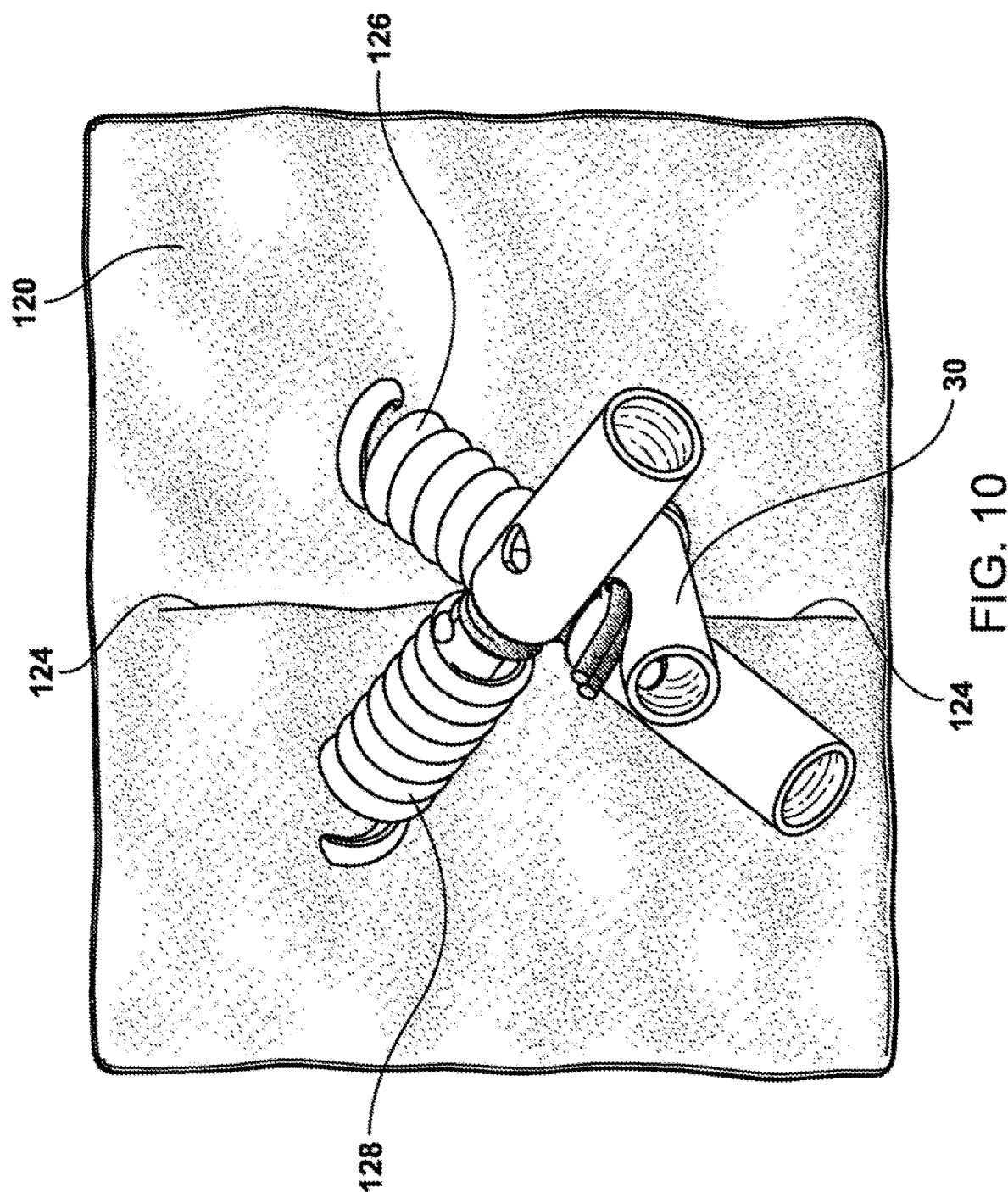
FIG. 10 is a perspective view of the helical tissue anchors and suture delivery components in a clinical setting whereby a defect in the tissues has been closed by manipulation of the delivery handle controls and retraction of the sutures attached to the two helical tissue anchors embedded within the side area of the tissue defect.

FIG. 10 is a perspective view of a pair of helical tissue anchors 128, 126 and suture delivery components 30 in a clinical setting whereby a defect 124 in intestinal mucosal, submucosal, or muscle tissues has been closed by manipulation of the delivery handle controls and retraction of the sutures attached to the two tissue helical anchors embedded within the side area of the mucosal or muscle tissues defect.

The Applicants anticipate that further developments and embodiments for a tissue anchor and delivery device with multiple tissue anchors in series within a catheter including a specifically designed apparatus to deploy series of anchors (details not shown in the Figures). In this additional embodiment, the tissue anchor(s) are deployed within the catheter in an extended or flat like form, then as they are pushed out of a constraining tube they immediately curl into a circular or helical-like configuration. Further modifications or embodiments for the tissue anchor device has at least two tissue anchors arranged in series within a catheter with a suture or suture like material affixed to the first or distal anchor then threaded through the eyelets of each following anchor(s). The suture is allowed to slide freely through the following anchors then the suture extends through the catheter and out the proximal end of the catheter such that the operator can grasp the end of the suture. A sliding crimp tie is positioned between every two anchors in series along the catheter. Once the first anchor is fired and affixed to tissue it exits the catheter, suture attached, moving the second anchor, with sliding but attached suture to the forward or distal end of the catheter. Once the second anchor is affixed to tissue the suture material connects these two affixed anchors and a sliding crimp tie also exits the catheter following the second anchor. The operator grasps the proximal suture end and pulls it with the crimp tie supported by the distal end of the catheter and slides the tie such that the anchors become close to each other and fixed in this configuration, whereby a defect would be closed. Two, three, four, or any number of anchors can be deployed in the same manner as described above to close a complex tissue defect.

Operation

The Operation Steps of the first embodiment for repairing wall defects and lesions are presented below.

Access and visualize the treatment area using standard endoscopy.

Advance the helical tissue anchor device through the working channel of the endoscope.

To engage one side of the treatment site, advance one of the thumb slides forward advancing and locking the first helical device and its delivery catheter out of the distal end of the catheter shaft at a desired length. The first helical device and its delivery catheter can be visualized by the endoscope.

Manipulate the scope and first tissue helical anchor and its delivery catheter to position the first tissue helical device against the first attachment target site.

Rotate a first thumbwheel to embed the first tissue helical device into the mucosal, submucosal or muscle tissue as desired.

Pull back on the first release mechanism to release the first helical device.

Push the central button on the first thumb slide to release the thumb slide allowing it to be pulled proximally.

Retract the thumb slide back, pulling the delivery catheter back into the sheath of the helical device leaving the first helical device attached to the suture strap mechanism embedded into the tissue.

To engage the other side of the lesion, advance and lock the second thumb slide forward advancing the second helical tissue anchor and its delivery catheter out of the distal end of the catheter shaft at a desired length. The second helical tissue device and its delivery catheter can be visualized by the endoscope.

Manipulate the scope and second helical tissue anchor and its delivery catheter to position the second tissue helical device against the second attachment target site.

Rotate the other thumbwheel to embed the second tissue helical device into the mucosal, submucosal, or muscle tissue as desired.

Pull back on the second release mechanism to release the second tissue helical device.

Push the central button on the second thumb slide down to release the thumb slide allowing it to be pulled proximally.

Retract the thumb slide back, pulling the delivery catheter back into the sheath of the helical device leaving the second tissue helical device attached to the suture strap mechanism embedded into the tissue.

Advance the entire device forward allowing the tensioned suture strap mechanism to pull the suture strap into outer sheath until the two anchors and the tissue defect walls are pulled together partially or fully closing the tissue defect.

Pull the proximal retraction finger grips back to initially lock the suture strap into the cinching and excising tubular member.

Continue to pull on the retraction finger grips to cut the suture strap and release the suture cinching and excising inner tubular member from the cinching member.

The device can then be removed from the endoscope leaving the tissue defect partially or fully closed by the cinched anchors.

In another embodiment of the device, the cinching mechanism could be a separate catheter. In this embodiment, the device is removed from the endoscope once the anchors are placed leaving suture strap mechanism in the endoscope channel.

By holding the central mandrel fixed and sliding the separate cinching device forward, a cinch, ferrell, bolo tie or spring or knot pushed with a knot pusher is pushed distally moving and locking the two helical anchors together thus, partially or fully closing the treatment area.

While this invention has been described as having a preferred design, the present invention can be further modified within the spirit and scope of this disclosure. The application is therefore intended to cover any variations, uses, or adaptations of the invention using its general principles. Further, this application is intended to cover such departures from the present disclosure as come within known or customary practice and the art to which this invention pertains and which fall within the limits of the appended claims.

The invention claimed is:

1. A method for repairing wall defects, plicating tissue, and treating lesions, applicable for a multiple helical device and delivery system, comprising:
   accessing and visualizing a treatment area using a standard endoscope;
   advancing a first tissue helical anchor and a second tissue helical anchor through a working channel of the standard endoscope;
   attaching the first tissue helical anchor to one side of a treatment site by advancing a forward motion mechanism to advance the first tissue helical anchor and a first delivery catheter out of a distal end of a catheter sheath;
   operating and manipulating the standard endoscope with the first tissue helical anchor and the first delivery catheter to engage the first tissue helical anchor against a first target site;
   embedding said first tissue helical anchor into a mucosal, submucosal or muscle tissue;
   releasing the first tissue helical device;
   retracting said first delivery catheter back into the catheter sheath;
   engaging another side of the treatment site by advancing the second tissue helical anchor and a second delivery catheter out of the distal end of the catheter sheath;
   operating and manipulating the standard endoscope and the second tissue helical anchor and the second delivery catheter to engage the second tissue helical anchor against a second target site;
   embedding the second tissue helical anchor into the mucosal, submucosal or muscle tissue;
   releasing said second tissue helical anchor;
   retracting said second delivery catheter back into the catheter sheath;
   sliding a central tube forward moving the first tissue helical anchor and the second tissue helical anchor together thus, partially or fully closing the treatment area; and
   holding the central tube forward and pulling back on a central mandrel lock to lock the first tissue helical anchor and the second tissue helical anchor and cut a strap or suture between the first tissue helical anchor and the second tissue helical anchor.

2. The method as recited in claim 1 further comprising a step of adjusting a depth of tissue capture when embedding said first and/or second tissue helical anchor.

3. The method as recited in claim 2, further comprising adjusting the depth of tissue capture enabling both full-thickness tissue closure and full-thickness plication.

4. A method for repairing wall defects, plicating tissue, and treating lesions, applicable for a multiple tissue anchor and delivery system, comprising:
   accessing and visualizing a treatment area using a standard endoscope;

advancing a first helical anchor device and a second helical anchor device through a working channel of the standard endoscope;

engaging one side of a treatment site, advancing a first thumb slide forward, and advancing the first helical anchor device and a first delivery catheter out of a distal end of a catheter shaft;

manipulating the standard endoscope and the first helical anchor device and the first delivery catheter to position the first helical anchor device against a first attachment target site;

rotating a first thumbwheel to embed the first helical anchor device into mucosal or muscle tissue as desired;

pulling back on a first release mechanism to release the first helical anchor device;

pushing a central button on the first thumb slide down to release the first thumb slide allowing it to be pulled proximally;

retracting the first thumb slide back, pulling the first delivery catheter back into the catheter shaft and leaving the first helical anchor device embedded into the mucosal or muscle tissue;

engaging another side of the treatment site, advancing a second thumb slide forward, and advancing the second helical anchor device and a second delivery catheter out of the distal end of the catheter shaft;

manipulating the standard endoscope and the second helical anchor device and the second delivery catheter to position the second helical anchor device against a second attachment target site;

advancing a sheath forward to move the first and second helical anchor devices together, thus partially or fully closing a tissue defect;

pulling or advancing a cinching mechanism to lock a suture holding the first helical anchor device and the second helical anchor device, and to lock walls of the mucosal or muscle tissue in a partially or fully closed state; and cutting the suture and releasing the cinching mechanism.

5. The method as recited in claim 4 further comprising adjusting a depth of a tissue capture when embedding said first and/or second helical anchor device.

6. The method as recited in claim 5, further comprising that adjusting the depth of tissue capture enables both full-thickness tissue closure and full-thickness plication.

* * * * *